United States Patent [19]

Batchelder et al.

[11] Patent Number: 5,037,202
[45] Date of Patent: Aug. 6, 1991

[54] MEASUREMENT OF SIZE AND REFRACTIVE INDEX OF PARTICLES USING THE COMPLEX FORWARD-SCATTERED ELECTROMAGNETIC FIELD

[75] Inventors: John S. Batchelder, Somers; Marc A. Taubenblatt, Pleasantville, both of N.Y.

[73] Assignee: International Business Machines, Corporation, Armonk, N.Y.

[21] Appl. No.: 547,735

[22] Filed: Jul. 2, 1990

[51] Int. Cl.$^5$ .............................................. G01N 15/02
[52] U.S. Cl. ..................... 356/336; 356/338; 356/335; 356/349; 356/364
[58] Field of Search ................ 356/39, 336, 335, 337, 356/338–343, 364, 369, 72, 345, 349, 351, 360, 361; 250/574

[56] References Cited

U.S. PATENT DOCUMENTS

| | | | |
|---|---|---|---|
| 4,284,355 | 8/1981 | Hansen et al. | 356/335 |
| 4,358,201 | 11/1982 | Makosch | 356/351 |
| 4,650,330 | 3/1987 | Fujita | 356/349 |
| 4,850,225 | 7/1989 | Chen et al. | 356/349 |

Primary Examiner—Richard A. Rosenberger
Assistant Examiner—Hoa Pham
Attorney, Agent, or Firm—Perman & Green

[57] ABSTRACT

An apparatus is described for classifying particles and includes an optical system for transmitting to a focal plane which includes at least one particle, two substantially parallel optical beams, the beams being initially mutually coherent but of different polarizations. The beams are displaced and focused in the focal plane. A further optical system is positioned in the path which the beam takes after depating from the focal plane and combines the beams so that a particle-induced phase shift in one beam is manifest by a change in elliptical polarization of the combined beams. A first detector is responsive to the beam's intensity along a first polarization axis to produce a first output and a second detector is responsive to the beams intensity along a second polarization axis to produce a second output. The first and second outputs are added to provide an extinction signal and, in a separate device, are subtracted to provide to phase shift signal. The extinction signal and phase shift signal are both fed to a processor which classifies a particle in accordance therewith.

12 Claims, 6 Drawing Sheets

PARTICLES ON BARE Si: λ = 633 nm, NA = 0.5

MEASUREMENT OF SIZE AND REFRACTIVE INDEX OF PARTICLES USING THE COMPLEX FORWARD-SCATTERED ELECTROMAGNETIC FIELD

FIELD OF THE INVENTION

This invention relates to the detection and characterization of small particles, and more particularly, to an improved method and apparatus for determining both the size and refractive index of a particle.

BACKGROUND OF THE INVENTION

Contamination control in the manufacture of semiconductors is ever increasingly important. Particulate contamination causes more than half of the yearly losses in volume semiconductor manufacturing. A substantial amount of this loss is due to chemicals such as solvents, acids, bases and process gases that come into contact with the wafers. The contaminant concentration in such fluids is typically more than three orders of magnitude greater than that present in clean room air and six orders of magnitude greater than that present in the next generation of clean rooms.

The prior art is replete with instruments and methods for detecting particles by measuring scattered light. Traditionally, such light scattering is measured by determining the scattered light intensity from a particle or collection of particles. The forward direction is always excluded due to the presence of the incident beam. It is known that the relationship between a forward scattered field from a small particle and the focused incident beam is such that light scattered by the particle causes both a phase shift and an attenuation of the incident beam. The latter of these is called the optical extinction effect.

In U.S. Pat. Application Ser. No. 07/184,639 entitled "Particulate Inspection of Fluids", by Batchelder et al. and assigned to the same assignee as this application, the phase shift experienced by an incident beam is employed to differentiate between bubbles and particles in a fluid. In that patent application, as well as in an article by the inventors which appeared in Applied Physics Letters, Vol. 55, No. 3, July 1989, pp. 215–217, it is shown that a small dielectric particle in a focused monochromatic light beam, produces a scattered wave in phase quadrature with the far-field incident beam, thereby causing a phase shift in the beam. The forward scattered field is detected using a bright field interferometer which measures the phase shift in one beam relative to another. As a particle enters the first beam, it causes a phase shift in that beam relative to the second, with the resulting signal passing through zero at a point between the two beams and then changing sign as the particle enters the second beam. Elliptical polarization results from the induced phase shift. The phase shift is detected by subtracting the optical energy oriented along the minor axis of the ellipse from the optical energy oriented along the ellipse's major axis.

In addition to contamination detection in fluids, it is important to detect particulate contamination of semiconductor surfaces. Various systems have been proposed for surface examination. An article by See et al. entitled "Scanning Differential Optical Profilometer for Simultaneous Measurement of Amplitude and Phase Variation", Applied Physics Letters, Vol. 53, No. 1, July 1988, pp. 10–12 describes a scanning optical profilometer which measures the differential phase/amplitude variations of light reflected off an object surface. The phase and amplitude of the reflected signals enable measurements of film thickness, reflectivity variations and surface flatness. The See et al. system employs a Bragg cell for interrogating the surface with two separate beams.

Heinrich et al. in "A Non-Invasive Optical Probe For Detecting Electrical Signals and Silicon IC's", Review of Progress in Quantitative NDE; edited by D. Thompson et al., Plenum Press, Vol. 7B, 1988, pp. 1161–1166, describe an optical probe system for detecting electrical signals in silicon integrated circuits. Carriers within the circuit perturb the index of refraction of the material and enable a Nomarski interferometer to detect such perturbations. In essence, Heinrich et al. detect a phase change between two optical beams focused on a surface being interrogated. Again, elliptical polarization results from the reflection of those beams and is detected in a differential sensing circuit Neither See et al. or Heinrich et al. apply their systems to particle detection or characterization.

The prior art systems mentioned in the above copending application enable a particle to be differentiated from a gas bubble and, in addition, enable the size of the particle to be estimated. But, in order to determine where contamination is originating, it would be useful if a particle could be further classified to enable it to be identified as to its composition. Knowing its composition will enable rapid identification of the source of the contaminant and its elimination.

Accordingly, it is an object of this invention to provide a system which classifies particles by a physical characteristic thereof.

It is still another object of this invention to provide a system for classifying particles in accordance with their complex refractive index.

It is still a further object of this invention to provide an improved system for classifying small particles in both fluid and solid environments.

SUMMARY OF THE INVENTION

An apparatus is described for classifying particles and includes an optical system for transmitting to a focal plane which includes at least one particle, two substantially parallel optical beams, the beams being initially mutually coherent but of different polarizations. The beams are displaced and focused in the focal plane. A further optical system is positioned in the path which the beams take after departing from the focal plane and combines the beams so that a particle-induced phase shift in one beam is manifest by a change in the elliptical polarization of the combined beams. A first detector is responsive to the beam's intensity along the first polarization axis to produce a first output and a second detector is responsive to the beam's intensity along a second polarization axis to produce a second output. The first and second outputs are added to provide an extinction signal and are subtracted to provide a phase shift signal. The extinction signal and phase shift signal are both fed to a processor which classifies a particle in accordance therewith.

DETAILED DESCRIPTION OF THE INVENTION

Figure 1:
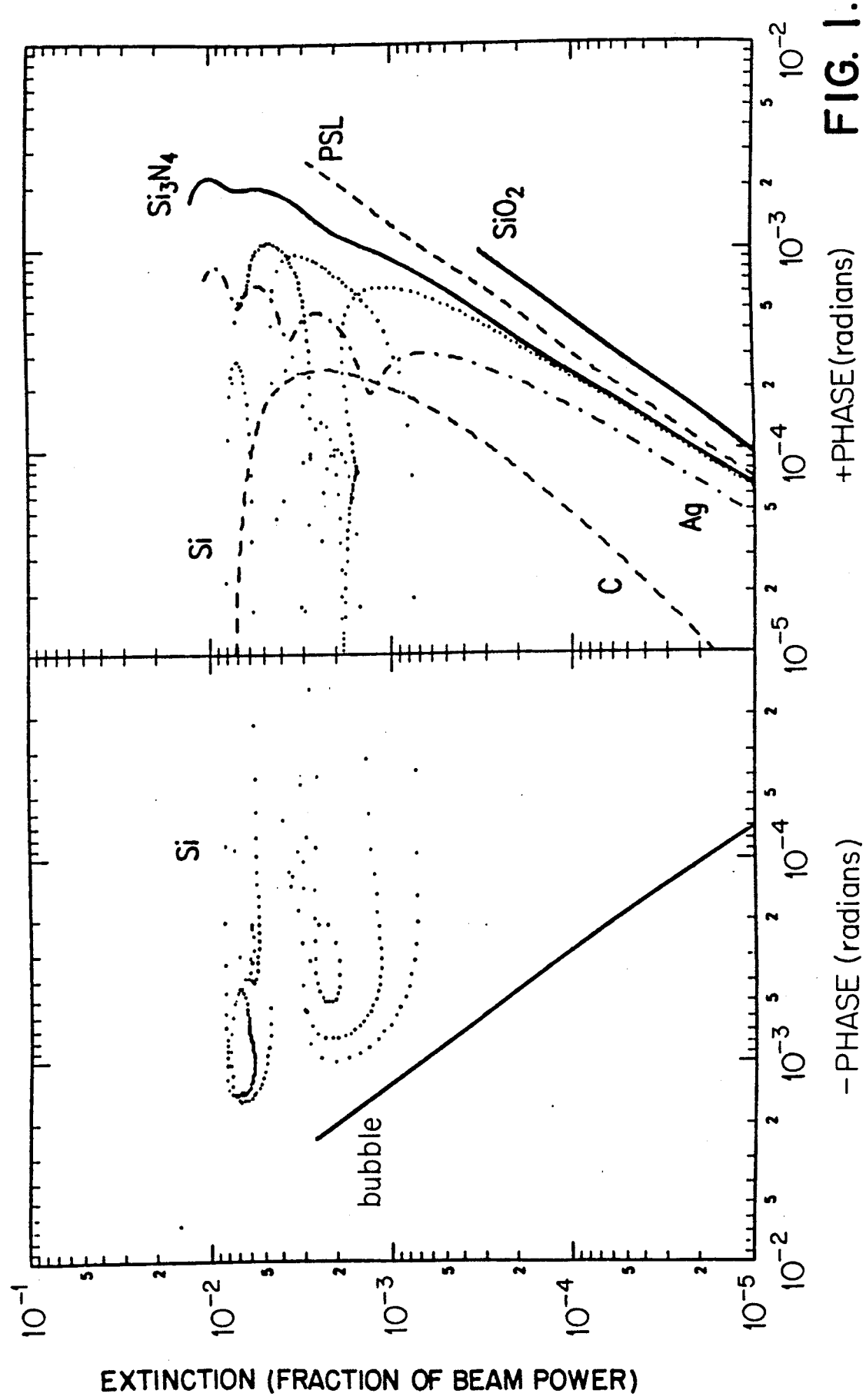
FIG. 1 is a plot of calculated extinction versus phase shift for particles exhibiting different refractive indices.

Prior to describing the apparatus which embodies this invention, a brief description of the theory which underlies its operation will be presented. The optical system described hereinbelow derives both phase shift and extinction arising from the presence of a particle in a focused, coherent beam. Those quantities have been found to correspond to the real and imaginary parts of the complex forward-scattered field of the beam. Such measurements enable information about a particle's size and its refractive index to be derived. The determination of refractive index is of particular value, as this information can lead to identification of the particle's composition and its probable source.

The effect of a particle on a focused beam can be derived by considering the outgoing beam to be a superposition of the incoming beam and the scattered wave from the particle. For a particle smaller than the wavelength of the focused beam, the scattered wave is real (no imaginary part), resulting in pure phase shift of the outgoing beam. If the particle considered is allowed to increase in size, such that additional terms of the Lorenz-Mie expansion of the scattered wave become important, or is allowed to be absorbing, it is found that both real and imaginary terms are present, leading to both phase shift and extinction of the focused beam. See "Absorption and Scattering of Light by Small Particles", C.F. Bohren et al , John Wylie & Sons, New York, 1983. The particle is placed at the focus of the beam and it is then considered how the scattered field from the particle interacts with the incident beam to produce the outgoing beam.

In the far-field, the scattered radiation has the form of a spherical wave. The incident beam also has the form of the spherical wave, but has undergone a phase retardation of $\pi/2$ between the focus and the far field. Calculation of the effect of a particle on the incident beam can be made by adding the far-field scattering to the incident beam to obtain the total outgoing beam.

As an approximation in the general case of a focused beam, the field amplitude of the "plane wave" at focus is given by $|E_o|^2 \times P/\pi\omega_0^2$ where P is the power in the beam and $\omega_o$ is the beam waist. Using the scattering amplitude matrix formulation, the scattered field is then a spherical wave, given by (the time dependent factor exp[−wt] is omitted):

$$E_{sc} = E_o \frac{\exp[ikR]}{-ikR} S(0°) \qquad (1)$$

where $E_o$ is the incident field at beam focus, $k = 2\pi n/\lambda$ is the wavenumber, $\lambda$ the vacuum wavelength, n the ambient refractive index, R the far-field radial distance, and S(0°) the scattering matrix function in the forward direction (which becomes polarization independent).

The incident beam in the far-field may be approximately given by:

$$E_{inc} = \frac{E_o \omega_o}{R \theta_{NA}} \exp[ikR - i\pi/2] \qquad (2)$$

where N.A. is the numerical aperture of the optical system $\theta_{NA} \cong \text{N.A.}/n$, and the amplitude factor is determined by conservation of power in the beam.

The outgoing beam is the sum of the scattered and incident beams in the far-field, and the scattered field component of the sum is much smaller than that due to the incident field.

It can be shown that the effect on the outgoing beam can be represented by a complex number which is proportional to the forward scattered field. The beam's phase shift is the real part of the complex number and is expressed by equation 3 and the imaginary part of the complex number represents the beam's extinction and is expressed by equation 4.

$$\text{extinction} = Im\left[\frac{iS(0°)}{2} \frac{N.A.^2}{n^2}\right] \qquad (3)$$

$$\text{phase} = Re\left[\frac{iS(0°)}{2} \frac{N.A.^2}{n^2}\right] \qquad (4)$$

The first few terms of the Lorenz-Mie expansion of S(0°) for small particles can be expressed as follows:

$$S(0°) = -i\frac{(m^2-1)}{(m^2+2)}x^3 - \qquad (5)$$
$$i\frac{(m^2-1)^2(38+27m^2+m^4)}{15(m^2+2)^2(2m^2+3)}x^5 + \frac{2(m^2-1)^2}{3(m^2+2)^2}x^6 + \ldots$$

Where m is the relative, complex, refractive index, (index of the particle divided by the index of the medium in which it is present) x = ka is the size parameter, and a is the particle radius. For a very small, non-absorbing particle (m is real), the largest term is the $x^3$ term, which is imaginary (i.e. iS(0°) is real) and therefore produces pure phase shift. The term is also proportional to the scattered field. Thus the total scattered intensity, which is equal to the extinction in this case, must be proportional to the square of this term, integrated over all angles, and therefore show the known $x^6$ dependence for very small particles.

The extinction may also be derived by examination of the first real term in the series, the $x^6$ term. This must also be related to the square of the $x^3$ term, a consequence of the optical theorem. For small absorbing particles, both the phase shift and the extinction will show a cubic dependence. For larger particles, the higher order terms contain both imaginary and real parts for non-absorbing as well as absorbing particles. It is the changing relationship of the Re[S(0°)] versus Im[S(0°)] as a function of m, that allows determination of refractive index.

The expected phase shift and extinction due to spherical particles have been calculated for a variety of materials in water for diameters of 0.1 to 0.5 microns and a vacuum wavelength of 0.633 microns, using the Lorenz-Mie theory. In FIG. 1, a plot of phase shift against extinction is shown for a variety of particles. Each curve is for a different material's refractive index and is plotted with particle size as a parameter. The indices of refraction (n) for the particles shown in FIG. 1 (at wavelengths of 633 nm) are as follows: Ag, $n=0.135+3.9i$; $SiO_2$, $n=1.43$; Polystyrene latex (psl), $n=1.59$; $Si_3N_4$, $n=2.0$; C, $n=2+0.7i$; Si, $n=3.85+0.018i$; air bubble, $n=1.0$; and $H_2O$, $n=1.33$.

The size of a particle can be inferred from its position on a curve in FIG. 1. The larger the particle, the further along the curve will occur its data point. The complex refractive index can be inferred from the particle-curve on which a particle's data point falls. For instance, for a low refractive index material, e.g., glass, light will not scatter to any great extent and thus the value for its extinction will be small compared to its phase shift. For a higher refractive index material, e.g., carbon, the extinction value will be higher due to the higher absorptivity of the material, (determinable from the imaginary part of the refractive index value).

From an examination of FIG. 1, it can be seen that there are many regions where both the size and refractive index may be uniquely determined for a subset of refractive indices. Thus, a single measurement of a particle-induced phase shift and extinction can be used to determine both its diameter and its complex refractive index (and thus its composition).

Figure 2:
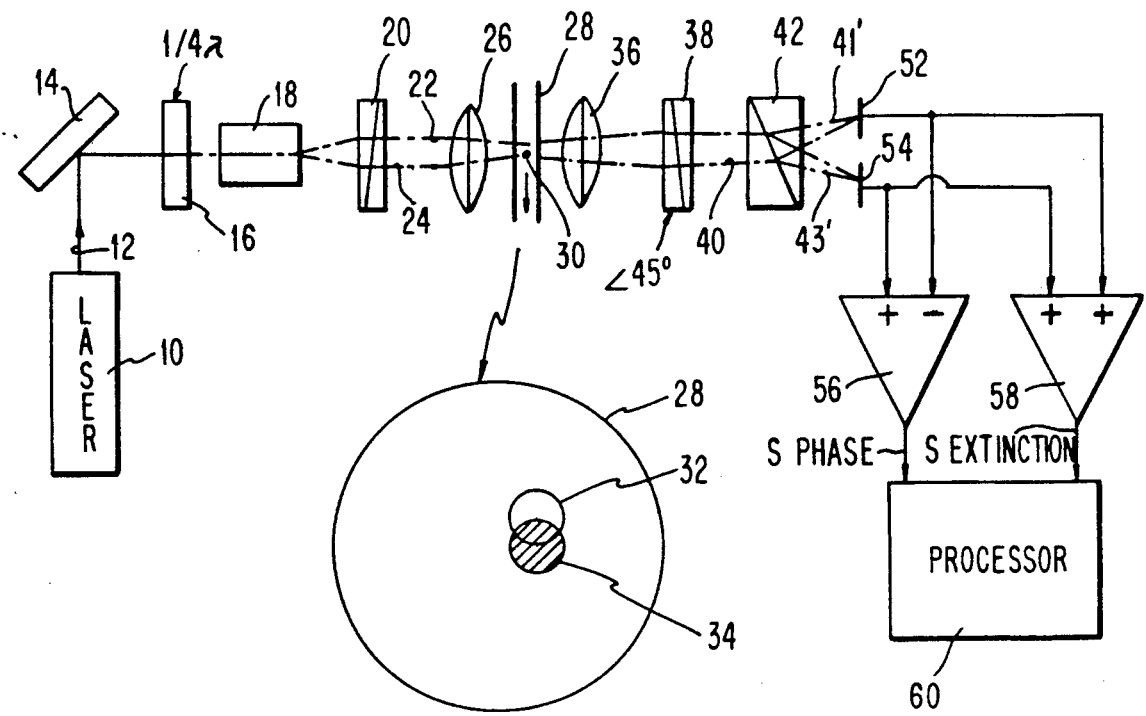
FIG. 2 is a schematic representation of a preferred embodiment of the invention for classifying particles in a fluid.
Figure 3:
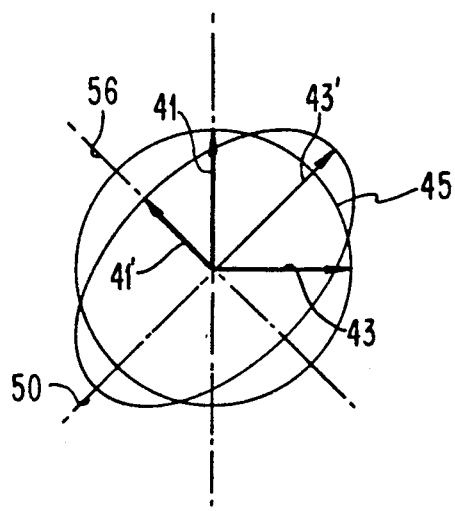
FIG. 3 is a plot of both circular and elliptical polarizations and is helpful in understanding the operation of the embodiment of FIG. 1.

Referring to FIGS. 2 and 3, a preferred embodiment is shown of the invention. A laser 10 directs its beam 12 to a mirror 14, where it is reflected and passes through quarter wave plate 16 to a beam expander 18. The expanded beam then enters a Nomarski wedge 20 where orthogonal polarization components are separated into two independent beams 22 and 24. For the purposes of this description, it will be assumed that beam 22 is vertically polarized and beam 24 horizontally polarized. Both beams are focused by lens 26 onto a flow cell 28 through which particle 30 passes. Lens 26 causes two independent, but substantially parallel, focused spots to appear at a focal plane which is substantially incident with the position of particle 30. Those spots are indicated as 32 and 34 in the expanded plan view of cell 28. A particle passing through spot 32 will cause a phase shift and a change in extinction of the focused beam but will not affect the phase of beam 24 until it enters into focused spot 34.

Once the two beams exit from cell 28, they pass through focusing lens 36 and enter a second Nomarski wedge 38. There, the beams are recombined into a single expanded beam 40.

If no particle was present in cell 28, the combined vertically and horizontally polarized light energies are equal and the result is a circularly polarized beam exiting from Nomarksi wedge 38. This is illustrated in FIG. 3 where vertical polarization 41 is shown equal to horizontal polarization 43, thus leading to a circular polarization 45. If, on the other hand, a particle 30 is present in the focal plane of one of the focused beams within cell 28, the beam experiences both a phase shift and a change in its extinction. The change in phase shift creates an elliptical polarization, wherein the difference between the axes of the ellipse is representative of the phase difference between one polarized beam (e.g. 22) and the other polarized beam e.g., 24). A change in extinction of one beam 22 with respect to the other beam 24 can be measured as a change in total power of the combined beams or as the intensity difference of polarization along the Nomarski axes.

The combined light beam 40 is passed to a Wollaston prism 42 which separates beam 40 into its polarization components at an angle of 45 degrees to the original Nomarski axes. This is illustrated in FIG. 3 by axes 50.

Beam 41' is directed at photo detector 52 (schematically shown), whereas orthogonally polarized beam 43' is directed to photodetector 54. Photodetectors 52 and 54 provide signals indicative of the intensity of incident beams 41' and 43' respectively. Outputs from photodetectors 52 and 54 are fed to subtractive operational amplifier 56 and to additive operational amplifier 58. The difference signal emanating from amplifier 56 ($S_{phase}$) may be expressed as:

$$S_{phase} = P(phase_1 - phase_2) \qquad (6)$$

where P is the incident laser beam power (with P/2 in each spot); $phase_1$ corresponds to the phase of spot 32 (beam 22) whereas $phase_2$ corresponds to the phase of spot 34 (beam 24).

The extinction signal is measured by using the output from summing amplifier 58 and the corresponding signal can be expressed as:

$$S_{extinction} = P(extinction_1 + extinction_2) \qquad (7)$$

wherein P is the incident laser beam power, and $extinction_1$ corresponds to the extinction seen from spot 32 (beam 22), and $extinction_2$ is the extinction derived from spot 34 (beam 24). Both of signals $S_{phase}$ and $S_{extinction}$ are passed to processor 60, after analog to digital conversion (not shown).

Figure 4:
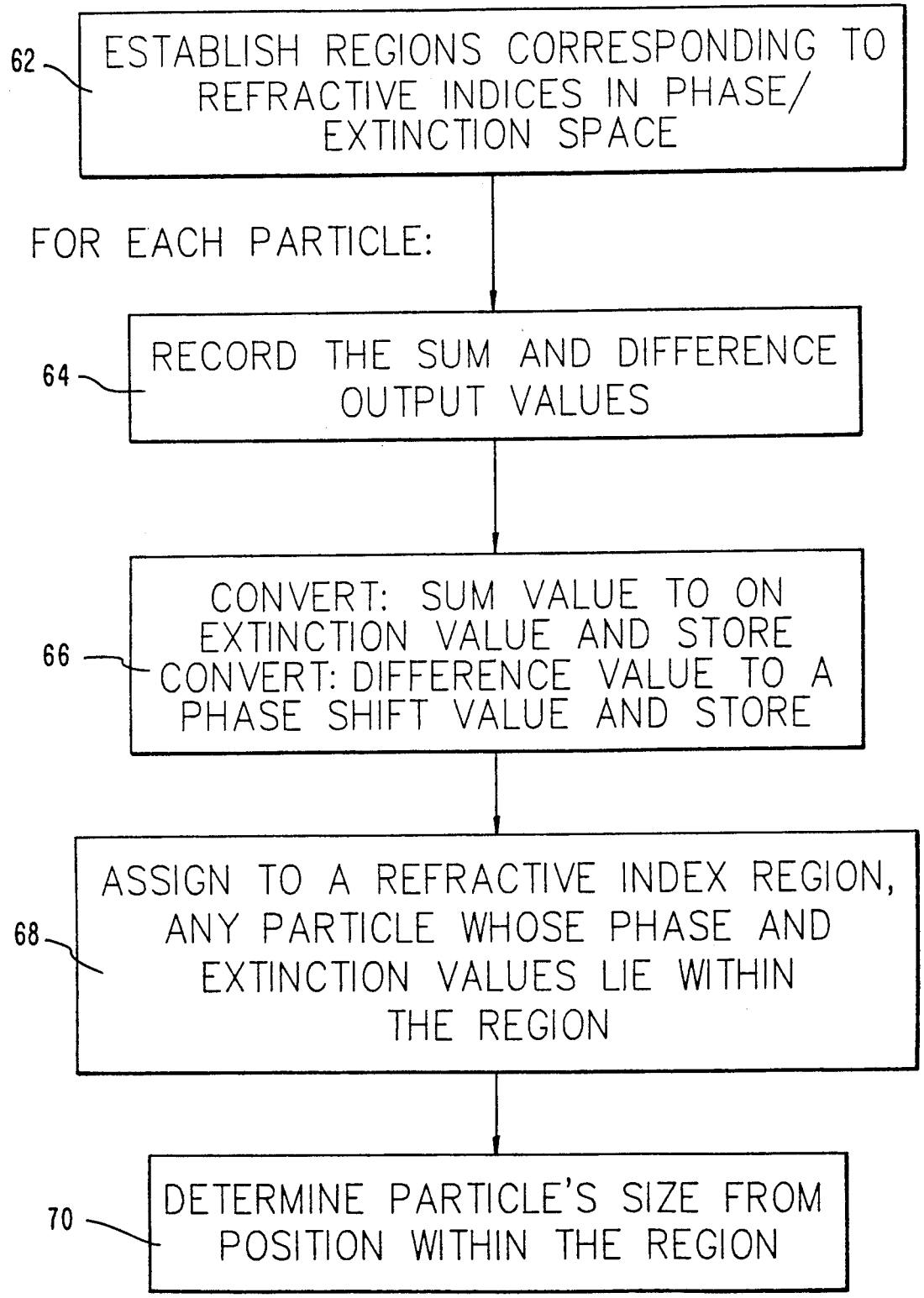
FIG. 4 is a high level flow diagram indicating the method of classification employed by the processor shown in FIG. 2.

The system described above, up to and through amplifier 56, (but not amplifier 58 and processor 60) is substantially as shown in prior, copending U.S. Pat. Application, Ser. No. 07/184,639 to Batchelder et al. What is not taught therein is that the $S_{phase}$ and $S_{extinction}$ signals can be employed to determine both the size of a particle and its refractive index. The processing of signals from amplifiers 56 and 58 in processor 60 will now be described in conjunction with the high level flow diagram of FIG. 4.

Initially, as shown in box 62, refractive index "regions" are established in the memory within processor 60 that correspond to refractive index values in a phase/extinction space or plane, (such as is shown in FIG. 1). In other words, areas in the plot are delimited as to phase shift value and extinction value so that regions are created corresponding to selected refractive indices. For instance, the positive phase-extinction plane can be divided into three regions, one corresponding to low refractive indices ($1.33 < n < 1.7$); a second corresponding to moderate refractive indices $1.7 < n < 2.7$ and a third corresponding to highly absorbing or metallic indices, $n > 2.7$.

Subsequently, as data corresponding to each particle is received, processor 60 records the sum and difference signal outputs from amplifiers 56 and 58 (box 64); converts each sum value to an extinction value, records it; and converts each difference signal to a phase shift value and records it (box 66). These conversions are accomplished by altering the signal values in accordance with scaling factors previously determined from similar measurements used to obtain phase and extinction values for particles of known size and refractive index.

Given the measured phase shift and extinction values, processor 60 then determines in which refractive index region each value falls and assigns these value to the determined region (box 68). By subsequently examining the refractive index region in which most of the particle data points are segregated, a user can begin to determine the composition of the particles by inference from the indicated refractive index region. Furthermore, the particle's size can be determined by the location of its data point within a refractive index region (box 70). As aforestated, its extinction and phase values will determine the place within the refractive index region in which the particle data point resides and thus the particle's size can be inferred.

Figure 5:
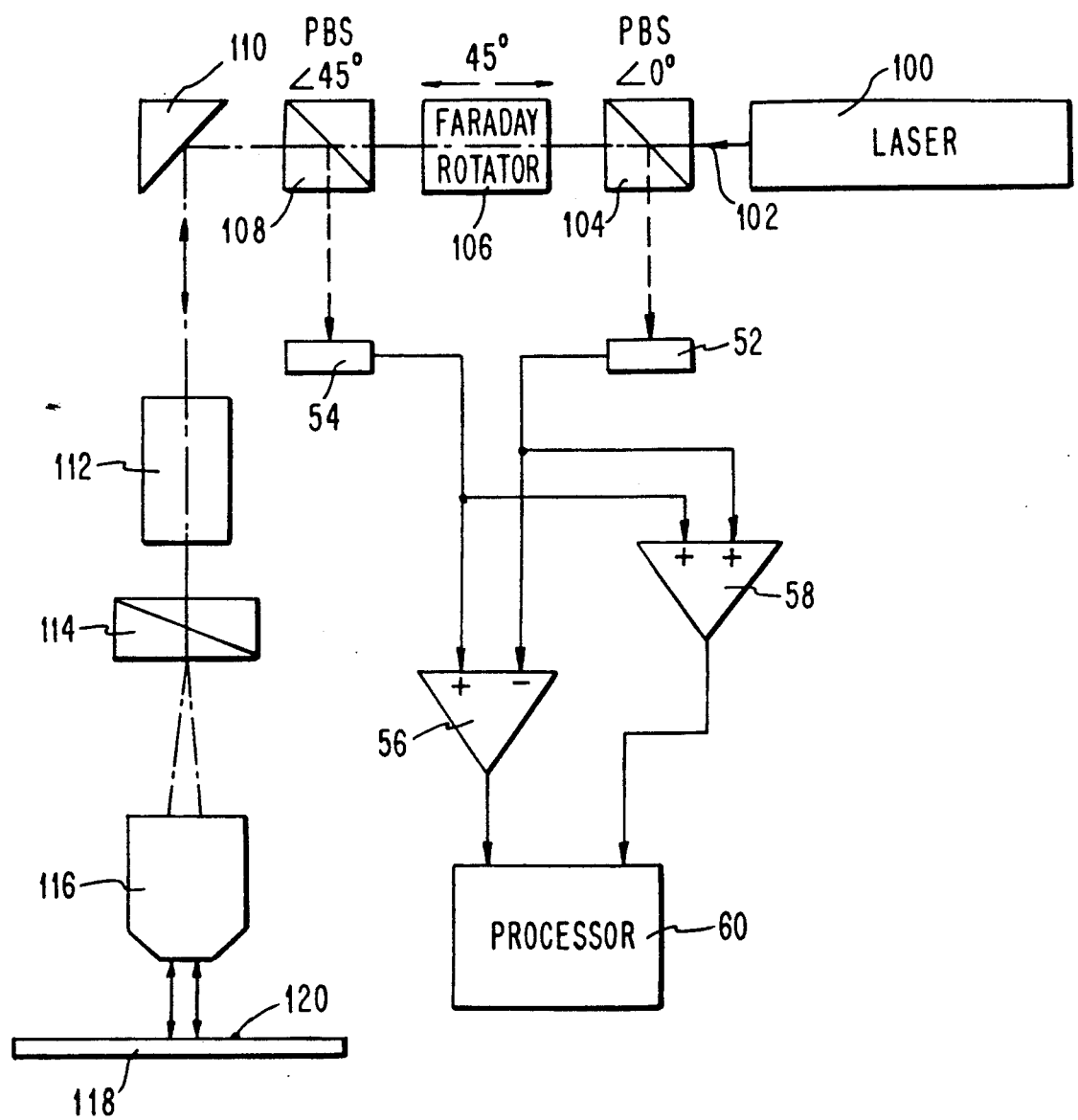
FIG. 5 is another preferred embodiment of the invention employed for classifying particles on a surface.

Turning now to FIG. 5, an optical system is shown, particularly adapted to sensing the extinction and phase resulting from a particle on a surface.

In FIG. 5, laser 100 produces a linearly polarized light beam 102 which passes through a first polarizing beam splitter 104. Polarizing beam splitter 104 has its polarization axis coincident with that of beam 102 as it exits from laser 100, and thus beam 102 passes therethrough without being affected. Beam 102 then enters a Faraday rotator 106 which rotates the beam's angle of polarization by 45 degrees. A Faraday rotator has the property of rotating the polarization of an incident beam in the same direction, no matter whether the beam enters from one side or the other side of the rotator. This function is employed herein and will be better understood below.

Beam 102 then passes to a second polarizing beam splitter 108 which is oriented at 45 degrees with respect to beam splitter 104. Here again, beam 102, exiting from Faraday rotator 106, passes through beam splitter 108 without being affected. Beam 102 is then reflected by mirror 110, passes through a beam expander 112 and enters a Nomarski wedge 114. There, beam 102 is split into two diverging, orthogonally polarized beams which enter a microscope objective 116 that focuses both beams on the surface of substrate 118. The presence of a particle 120 on substrate 118 causes both a change in the phase shift and extinction of the beam which falls on the particle. One beam acts as the reference, while the other is the signal beam.

The reflected beams proceed back through the optical system with Nomarski wedge 114 recombining them and causing a 90° phase difference between the combined polarizations so that the returning beam is circularly polarized (if no phase shift has occurred). On the other hand, if a phase shift in one beam has occurred, the beam is elliptically polarized. Polarizing beam splitter 108, Faraday rotator 106 and polarizing beam splitter 104 now direct one polarization which is 45 degrees to the polarization orientation of Nomarski wedge 114, to detector 54 and the orthogonal polarization to detector 52. The signals emanating from detectors 52 and 54 are processed identically to those as described for FIG. 2.

The surface of substrate 118 may be scanned by providing relative motion between the substrate and the interrogating beams. This may be accomplished by mounting substrate 118 on an x-y stage or by scanning the interrogating beams by a rotating mirror or other instrumentality.

Figure 6:
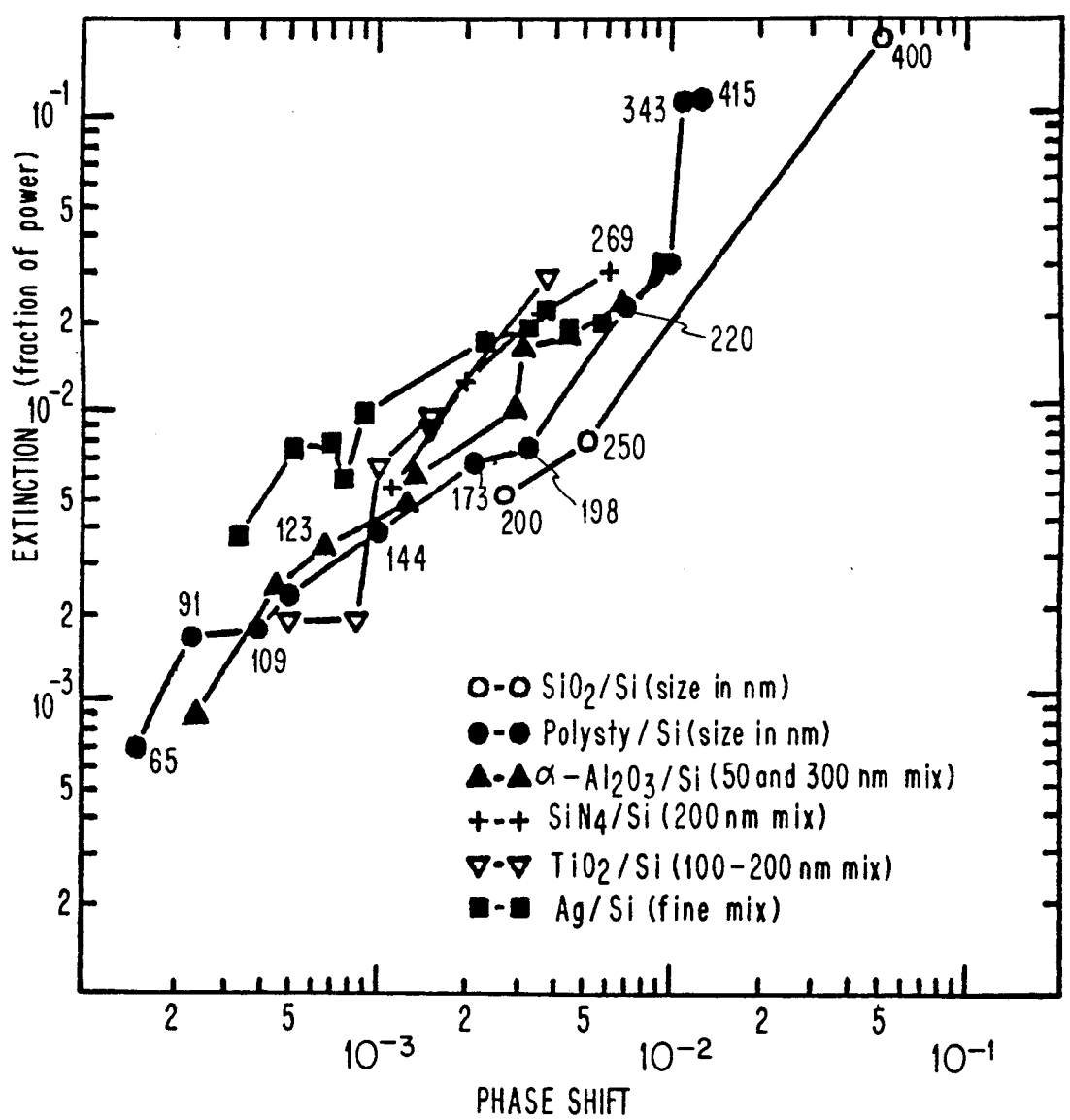
FIG. 6 is a plot of extinction versus phase shift for various particles on a bare silicon substrate.

Referring now to FIG. 6, a plot is shown of phase shift versus extinction for a plurality of indicated particle types on a bare silicon substrate. This data indicates that refractive index regions can be defined which segregate $SiO_2$ particles from polystyrene particles, etc. It can also be seen that there are some regions where an overlap of data points indicates that for certain particle sizes, ambiguities will arise—e.g. certain portions of the $Al_2O_3$ and Ag data points overlap. In such cases, statistical methods can be employed to differentiate between these particulates, by plotting a histogram of particles received over a period of time to determine in which region a majority of the particles reside. The numbers plotted in FIG. 6 indicate the size of certain of the particles in nanometers.

Figure 7:
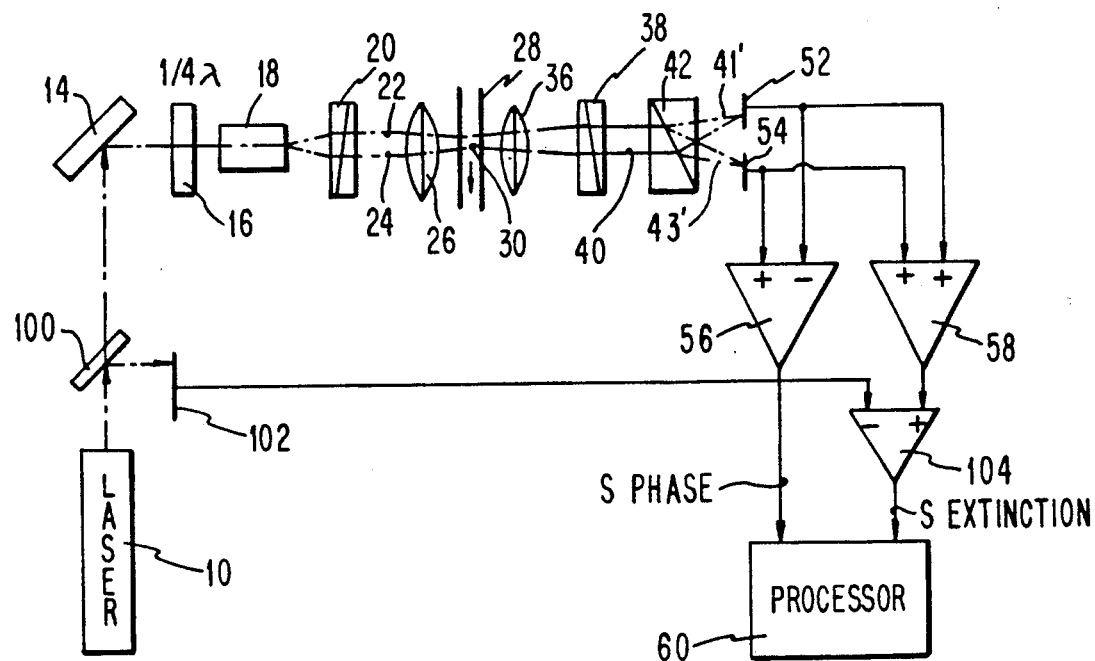
FIG. 7 is a schematic representation of an embodiment of the invention which enables a differential measure of extinction.
Figure 8:
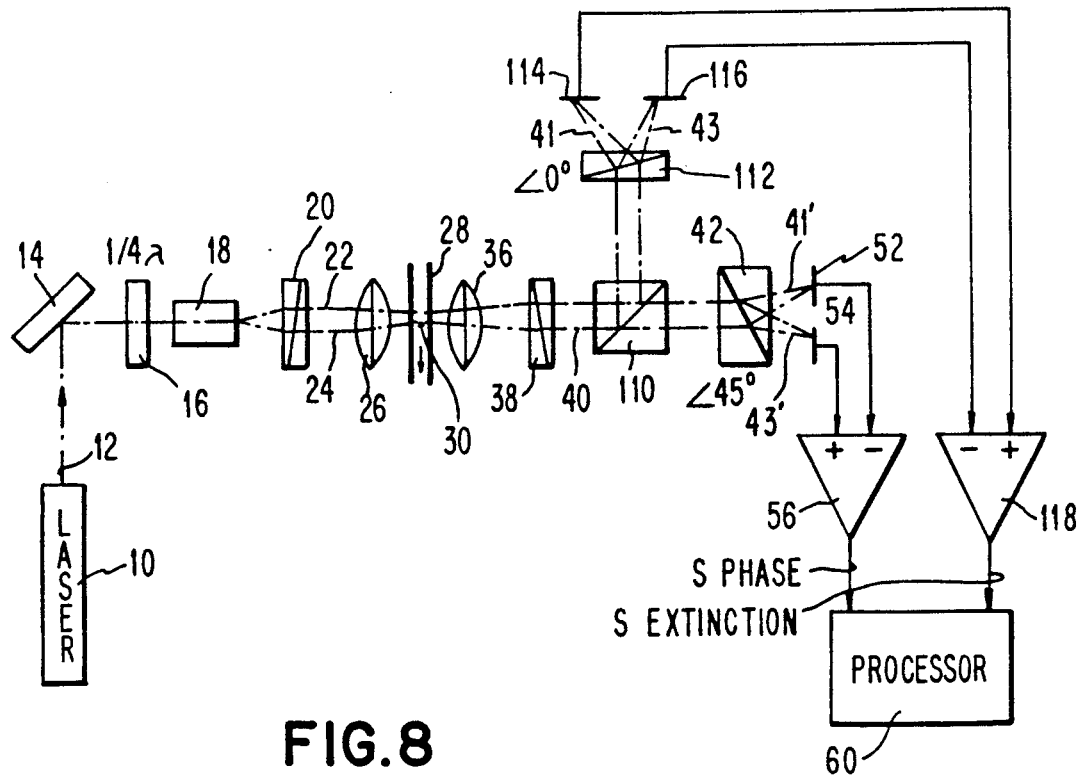
FIG. 8 is a schematic representation of another embodiment of the invention which enables a differential measure of extinction

As is apparent from the above description, the phase signal measurement is a differential measurement. Any phase or intensity changes which affect both beams equally (which might be due to laser noise, vibrations) will be subtracted out. The extinction signal is not, however, a differential measurement, thus changes in laser power (i.e. laser noise) will be measured as well as the extinction signals. While the phase signal is the more sensitive of the two because many more phenomena can cause phase changes (air turbulence, vibration) than intensity changes, it is still beneficial to the extinction measurement to make it differential as well. FIGS. 7 and 8 indicate system modifications which enable such a differential measurement.

In FIG. 7 a beam spitter 100 diverts a small fraction of the laser power to detector 102 as a measure of the laser power noise. This signal is then subtracted from the extinction signal (from amp 58) by using differential amplifier 104. Thus the laser power noise is monitored, and subtracted from the extinction signal.

In FIG. 8 a beam splitter 110 allows half of combined beam (40) to pass to Wollaston prism 42 where its axes are rotated by 45 degrees to the Nomarski axes, which enables measurement of the phase in the differential amplifier 56, as before. The other half of beam 40 is diverted to a second Wollaston prism 112 which is oriented with its axes parallel (0 degrees) to the Nomarski axes. Wollaston prism 112 separates the combined beam back into the polarization components corresponding to beams 22 and 24. Thus the extinction of one beam 22 with respect to the other beam 24 will be measured directly by the difference in intensity between beams 41 and 43, whose intensities are measured by detectors 114 and 116 and differenced by amplifier 118.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

We claim:

1. An apparatus for classifying particles comprising:
   means for transmitting to a focal plane that includes at least one said particle, two substantially parallel optical beams, said beams being initially mutually coherent but of different polarizations, said beams displaced and focused in said focal plane, said particle inducing a phase shift and change in intensity in one beam;

recombining means positioned in a path which said beams take after departing from said focal plane for combining said beams, a phase shift in said one beam causing said combined beam to manifest an elliptical polarization, and then separating said elliptically polarized combined beam into at least two beams, one having a first polarization axis and a second having a second polarization axis;

a pair of detector means, one said detector means responsive to said one beam's intensity to produce a first output, and another said detector means responsive to said second beam's intensity to produce a second output;

means for adding said first and second outputs to provide an extinction signal;

means for subtracting said first and second outputs to provide a phase shift signal; and processing means for classifying said particle in accordance with said extinction and phase shift output signals.

2. The apparatus as recited in claim 1 wherein said first and second polarization axes are coincident, respectively, with minor and major axes of said elliptical polarization.

3. The apparatus as recited in claim 1, herein said processing means includes means for establishing a phase shift/extinction space, and means for segregating a particle into said phase shift/extinction space in accordance with extinction and phase shift signals derived from said particle 4. The apparatus as recited in claim 3, wherein said processing means further includes means for allocating portions of said phase shift/extinction space to correspond with predetermined ranges of particle refractive indices, whereby a particle can be identified by reference to the particle's indicated refractive index.

5. The apparatus as recited in claim 4 wherein said processing means includes means for determining a particle's size from the particle's position in the phase shift/extinction space.

6. The apparatus as recited in claim 5 further comprising a transparent cell for confining said particle, said focal plane being within said transparent cell.

7. The apparatus as recited in claim 5 wherein said focal plane is coincident with the surface of a substrate on which said particle resides.

8. The apparatus as recited in claim 1 further comprising:

means for deriving a signal proportional to noise appearing in said optical beams and subtracting said proportional signal from said extinction signal to obtain a differential extinction signal.

9. An apparatus for classifying particles comprising:

means for transmitting to a focal plane that includes at least one said particle, two substantially parallel optical beams, said beams being initially mutually coherent but of different polarizations, said beams displaced and focused in said focal plane, said particle inducing a phase shift and change in intensity in one beam;

Nomarski optical means positioned in a path which said beams take after departing from said focal plane for combining said beams, a phase shift in said one beam causing said combined beam to manifest an elliptical polarization;

a first Wollaston optical means for separating said elliptically polarized combined beam into a first pair of beams, one having a first polarization axis and a second having a second orthogonal polarization axis, said axes being displaced by 45° from axes of said beams from said Nomarski optical means;

a second Wollaston optical means for separating said elliptically polarized combined beam into a second pair of polarized beams, the axes of said second pair of polarized beams coincident with polarization axes of said beams from said Nomarski optical means;

a first pair of detector means responsive to said first pair of polarized beams, one said detector means responsive to one beam's intensity to produce a first output, and another said detector means responsive to another second beam's intensity to produce a second output;

a second pair of detector means responsive to said second pair of polarized beams, one said detector means responsive to one beam's intensity to produce a third output, and another said detector means responsive to another beam's intensity to produce a fourth output;

means for subtracting said first and second outputs to provide a phase shift signal;

means for subtracting said third and fourth outputs to provide an extinction signal; and processing means for classifying said particle in accordance with said extinction and phase shift output signals.

10. A method for classifying particles by reference to their refractive index, said method employing an optical system which focuses a pair of orthogonally polarized, adjacent, coherent beams into a focal plane containing said particles, a particle causing a change in phase and intensity of one said beam with respect to another said beam, said beams being recombined into an elliptically polarized beam which is subsequently analyzed by respectively subtracting and adding optical energy aligned along one polarization axis and optical energy aligned along an orthogonal polarization axis, said subtracted energies being representative of a phase shift value and said added energies being representative of an extinction value, all as created by a said particle, the method comprising:

establishing a phase shift/extinction space;

determining a point in said space for said particle in accordance with said phase shift and extinction values;

allocating portions of said space to refractive index value ranges; and identifying a respective index of refraction range for said particle from said particles determined point in said space.

11. The method as defined in claim 10 wherein said allooated portions of said space correspond to refractive index values of expected contaminant particles.

12. The method as defined in claim 11 further including the step of:

determining a particle's size from the particle's point in said space.

* * * * *